United States Patent [19]

Malone

[11] Patent Number: 5,109,029

[45] Date of Patent: Apr. 28, 1992

[54] FRAGRANT THERMOPLASTIC FOAM AND METHOD OF MAKING THE SAME

[75] Inventor: Bruce Malone, Granville, Ohio

[73] Assignee: The Dow Chemical Company, Midland, Mich.

[21] Appl. No.: 592,010

[22] Filed: Oct. 2, 1990

[51] Int. Cl.$^5$ ............................................. C08G 18/14
[52] U.S. Cl. ...................................... 521/79; 521/82; 521/99
[58] Field of Search ............................. 521/79, 82, 99

[56] References Cited

U.S. PATENT DOCUMENTS 3,912,667  10/1975  Spitzer et al. .......................... 521/88

Primary Examiner—Maurice J. Welsh

[57] ABSTRACT

Substantially closed-cell thermoplastic foams having a fragrance incorporated into the foam during extrusion are found to provide fragrant and long lasting release characteristics provided the foam is at least 70 percent closed cells. Generally the amount of fragrance is about 0.001 to about 5 weight percent of the total thermoplastic foam weight.

18 Claims, No Drawings

FRAGRANT THERMOPLASTIC FOAM AND METHOD OF MAKING THE SAME

BACKGROUND OF THE INVENTION

The present invention relates to novel substantially closed-cell fragrant thermoplastic foams and method of making these fragrant thermoplastic foams.

Thermoplastic foams presently have a variety of uses, such as package cushioning, furniture cushioning and thermal insulation.

Generally thermoplastic foams (referred to as "foam" or "foams" in this specification) are produced by feeding a combination composed of a thermoplastic resin and other additives, such as a cell size controlling agent into an extruder, melting the composition under heat to a molten gel, adding a volatile blowing agent to the molten gel, and extruding the resultant molten gel containing the volatile the blowing agent through a die at the end of an extruder into an area having a lower pressure than the pressure inside the extruder.

Thermoplastic foams may be classified as open cell (or pore) and closed cell. The present invention is directed to those thermoplastic foams which are substantially closed cell.

One drawback to some foams is that an odor, which does not quickly dissipate, may be associated with or released by foams and remain detectable for an extended period of time. Some people may find these odors unpleasant. To counteract or overcome this odor released by polyurethane or other synthetic foams having a volatile component which is released over a period of time, artisans added a pleasing scent to the porous foam, including foam rubber. The prolonged release of the fragrance in certain products such as cushions is particularly desirable. Heretofore, however, the scents or fragrances added tend to dissipate quickly and then the original objectionable odor becomes dominant throughout the environment.

It has been known for some time to impregnate articles, having a high degree of porosity, with materials, preferably in the form of liquids, that will evaporate slowly at normal temperatures and pressures and thus permeate the adjacent atmosphere. Further, various sustained release means comprising a polymeric carrier have been proposed, i.e., U.S. Pat. Nos. 3,857,932; 3,975,350 and 4,202,880. Among the materials that may be impregnated into porous materials have been medications, perfumes, deodorants, germicides, pesticides, disinfecting and sterilizing agents, etc.

It is also known to the compounding art that agents not soluble within a thermoplastic polymeric matrix will not move at an efficacious rate through the matrix to the matrix surface and then enter the ambient environment. Solubility is not generally a problem wit an open cell foam. However a substantially closed cell foam behaves much like a nonfoamed thermoplastic resin in that the incorporated fragrance must move at an efficacious rate through the closed cell foam matrix to the foam surface and then enter the ambient environment. With substantially closed cell foams each cell wall is a new barrier to be crossed for the incorporated fragrance. Thus the incorporation of the fragrance into a substantially closed cell foams greatly increases the overall time for the release of the fragrance to the ambient atmosphere.

U.S. Pat. No. 4,339,550 discloses hydrophillic polyurethane foam products characterized by a cross-linked, non-linear molecular network which incorporate active materials, utilizing in situ methods, into the cell structure of the hydrophillic polyurethane foam so that the active material has a controlled release.

U.S. Pat. No. 4,254,179 describes how to overcome new carpet and foam underlay odor by impregnating the padding with a lasting fragrance, either in the form of an encapsulated fragrance which is slowly released as the foam is later used or a slow release fragrance which is long lasting due to the manner in which it is incorporated in the foam. The foam underlay in the form of a planar sheet is impregnated with a fragrance by application of particles carrying a fragrance to one major surface of the foam sheet. Heat may be applied to the underlay to cause the particles to migrate into the body of the foam. A vacuum is applied to the opposite surface of the foam causing the particles to migrate further into the foam. In addition, mechanical spreading of the particles as by brushing or wiping may be used to distribute the particles across the foam surface and into open voids in that surface. Finally, a semi-pervious layer may be bonded to the foam surface over the particles to retain them in place. In this manner a long lasting fragrant porous foam product is obtained.

These teachings however do not teach a fragrant substantially closed cell thermoplastic foam or a method for making this foam.

SUMMARY OF THE INVENTION

In the present invention, it has been surprisingly found that an extremely minor amount of a fragrance when incorporated into a substantially closed cell thermoplastic foam (a foam having seventy percent (70%) or greater closed cells) produces a fragrant substantially closed cell thermoplastic foam product whose scent does not quickly diminish.

Also in the present invention, it has been surprisingly found that this extremely minor amount of a fragrance can be added directly, as a concentrate or in other timed or controlled release form as an additive into a process producing a substantially closed cell thermoplastic foam to produce a substantially closed cell fragrant thermoplastic foam product whose scent does not quickly diminish.

In one preferred embodiment the fragrance is added as a concentrate where the fragrance is concentrated in thermoplastic polymer resin particles to be blended with the thermoplastic polymer resin particles used to make the substantially closed cell thermoplastic foam production. It is not required, due to the small amount of polymer in the fragrance/polymer concentrate, that the concentrate polymer or fragrance be soluble or miscible with or blend with the thermoplastic polymer resin particles used to make the substantially closed cell thermoplastic foam production, but it is preferable.

DETAILED DESCRIPTION

The foams of the present invention are those substantially closed cell thermoplastic polymer resin foams generally known in the art.

The thermoplastic polymers, that is polymers which soften and flow when heat and/or pressure is applied (the changes being reversible), are well known to the art and are readily set forth in various references such as textbooks, journals, various encyclopedias, and the like, as for example, the various thermoplastics set forth in the MODERN PLASTICS ENCYCLOPEDIA, 1979-1980, Vo. 56, 10A, McGraw-Hill, as well as in other years, and the like, which are hereby fully incorporated by reference. Furthermore, the various properties thereof are well known as are the molecular weight distributions. For example, the number average molecular weight can range from about 10,000 to about 1,000,000, desirably from about 40,000 to about 500,000, and preferably from about 60,000 to about 250,000.

Various thermoplastics can be utilized so long as a substantially closed cell foam is formed.

Generally, thermoplastics which can be used include the various following thermoplastics, as well as common copolymers, terpolymers or interpolymers thereof. The various polyolefins containing from 2 to 10 carbon atoms. Specific examples include polyethylene, such as low density and high density polyethylene. Typically, low density polyethylene has a partially (approximately 50 to approximately 60 percent) crystalline solid structure, whereas high density polyethylene typically has over a 90 percent crystalline structure. Polypropylene can also be utilized. Additionally, various copolymers of ethylene may be utilized such as ethylene-propylene, and copolymers of ethylene and vinyl acetate.

Also as suitable thermoplastic resins comprising, in polymerized form, a nonaromatic olefin there may be utilized copolymers of ethylene and a copolymerizable polar monomer especially a carboxyl-containing comonomer. Examples include copolymers of ethylene and acrylic acid or methacrylic acid and C1-4 (1-4 carbon atoms) alkyl ester or ionomeric derivatives thereof: ethylene vinyl-acetate copolymers; ethylene/carbon monoxide copolymers; anhydride containing olefin copolymers; copolymers of ethylene and an alpha-olefin having ultra low molecular weight (i.e. densities less than 0.92); blends of all of the foregoing resins: blends thereof with polyethylene (high, intermediate or low density); etc. Particularly preferred thermoplastic compositions are copolymers of ethylene and acrylic acid, (EAA copolymers) having up to about 30% by weight of copolymerized acrylic acid; ionomeric derivatives of the foregoing, copolymers of ethylene and vinyl acetate; ultra low density polyethylene; and blends of the foregoing with one another and with low density polyethylene.

The polymers of ethylene and a polar comonomer may be prepared by known addition polymerization techniques, or by a grafting reaction of the reactive comonomer with a preformed polymer of ethylene. Additional elastomeric components such as polyisobutylene, polybutadiene, ethylene/propylene copolymers, and ethylene/propylene/diene interpolymers may be included in the blend if desired but are not preferred. Moreover, additional components such as crosslinking agents designed either to provide latent crosslinking of the ethylenic polymer, such as silane functional crosslinking agents or covalent or ionic crosslinking agents, may be included if desired.

A preferred resin composition comprises a copolymer of ethylene and acrylic acid or ethylene and vinyl acetate containing from about 60 percent to about 95 percent with a range of from about 80 percent to about 93 percent being more preferred and a range of from about 85 percent to about 98 percent being most preferred. The weight average molecular weight of the copolymer generally ranges from about 40,000 to about 400,000 and preferably from about 75,000 to about 300,000. Desirably, the copolymer has an ASTM Test #D1238 melt flow index of from about 6 to about 12 and preferably from about 7 to about 11 and a Vicat softening point of from about 70° C. (degrees centigrade) to about 95° C. A preferred thermoplastic composition is a homogeneous, random copolymer of ethylene and acrylic acid (EAA copolymers) having up to about 30% by weight of copolymerized acrylic acid: ionomeric derivatives of the foregoing, copolymers of ethylene and vinyl acetate; ultra low density polyethylene; and blends of the foregoing with one another and with low density polyethylene. Copolymers of ethylene and acrylic acid or of ethylene and vinyl acetate may be obtained from The Dow Chemical Company. Ethylene vinyl acetate copolymers may also be obtained under the tradename Elvax from E. I. duPont deNemours & Company. Anhydride modified copolymers of ethylene are available under the tradename Plexar from Norchem, Inc. Ionomeric copolymers are available under the tradename Surlyn (Registered TM) from E. I. duPont deNemours & Company.

An example of an ethylene-propylene copolymer is those having a weight average molecular weight of from about 50,000 to about 250,000 with a preferred range of from about 100,000 to about 200,000. The percent by weight of the ethylene units can generally vary from about 30 percent to about 80 percent and preferably from about 45 percent to about 75 percent. The melt flow index of the ethylene-propylene copolymer can generally range from about 15 to about 45, and preferably from about 20 to about 32 according to ASTM Test #1238 at 190°, 21600 gm,gm/10 minutes.

Polystyrene can be utilized as well as a family of styrene polymers which includes copolymers of styrene with other vinyl monomers or vinyl substituted aromatics having from 8 to 12 carbon atoms, polymers of derivatives of styrene, and the like. Thus, poly-alpha-methylstyrene may be utilized. Another group of thermoplastic polymers is the acrylic polymers with specific examples being polyacrylate, polymethylacrylate, and polymethylmethacrylate. The polyvinyl esters constitute yet another group with a specific example being polyvinylacetate. Still another group is the polyvinyl acetals such as polyvinylbutyral. The phenylene oxide-based thermoplastics can also be used. The various chlorine-containing polymers can be utilized such as polyvinylchloride, polytetrafluoroethylene, polychlorotrifluoroethylene, polyvinylfluoride, polyvinylidenefluoride, and the like. These polymers are used without plastication.

The polyamides or nylons are another group of thermoplastics and include Nylon 6, Nylon 10, Nylon 11, Nylon 12, Nylon 6,6, Nylon 6,10, and the like.

Polyethers such as polyoxymethylene can be utilized.

Another large group of thermoplastic compounds are the polyesters such as polyethylene terephthalate, polybutylene terephthalate, and the like. The thermoplastic polyurethanes constitute yet another group of thermoplastics. As known to those skilled in the art, the thermoplastic polyurethanes can be made from several types of polymers or prepolymers. The cellulose plastics are yet another group with specific examples being cellophane and rayon.

Preferred thermoplastics include polyethylene, including low, intermediate and high density polyethylene, linear low density polyethylene, copolymers of ethylene-vinyl acetate, copolymers of ethylene-acrylic acid, polypropylene, polybutylene, polystyrene, poly-alpha-methyl styrene, polymethylacrylate, polyacrylate, polymethylmethacrylate, polyvinyl acetate, polyvinyl butyral, polyvinyl chloride, polytetrafluoroethylene, polychlorotrifluoroethylene, polyvinyl fluoride, a copolymer of ethylene-propylene, polyvinylidene fluoride, Nylon-6, Nylon-6,6, Nylon-6,10, polyoxymethylene, polyethyleneterephthalate, cellophane, rayon, and combinations thereof.

The most preferred thermoplastics include polyethylene (including low, intermediate or high density polyethylene and linear low density polyethylene); a homogeneous, random copolymer of ethylene and acrylic acid (EAA copolymers) having up to about 30% by weight of copolymerized acrylic acid; ionomeric derivatives of the foregoing, copolymers of ethylene and vinyl acetate; ultra low density polyethylene; blends of the foregoing with one another and with low density polyethylene; polystyrene; and other combinations thereof.

Volatile blowing agents include known blowing agents such as a chlorofluorocarbons, e.g., 1,2-dichlorotetra-fluoroethane, 1,2-difluorotetrachloroethane, chlorotrifluoromethane, 1-chloro-1,1-difluoroethane and mixtures thereof with additional agents such as halogenated hydrocarbons, hydrocarbons, carbon dioxide, water, etc. Particularly preferred as a blowing agents with olefin polymers is isobutane and isobutane combinations described in U.S. Pat. No. 4,964,027.

Additional agents such as nucleating agents, extrusion aids, antioxidants, colorants, pigments, etc. may also be included in the blend as desired.

For the purpose of definition in this specification, the term substantially closed cell means that at least seventy percent (70%) or greater of the cells in a single piece, or in the case of coalesced foam each single strand, are closed. Preferably at least eighty percent (80%) or greater of the cells are closed. Most preferably at least ninety percent (90%) or greater of the cells are closed.

One common method of measuring the open cell content of rigid cellular plastics is by an air pycnometer. ASTM D 2856-87 (American Society for Testing and Materials, Philadelphia, Pa., USA) provides the details one common test procedure for determining porosity. The test method is based on a determination of porosity in which the accessible cellular volume of a cellular plastic is determined by application of Boyle's Law, which states that the decrease in volume of a confined gas results in a proportionate increase in pressure.

For this test method a foam sample of known exterior volume is placed in a sealed containment of known volume. A piston on the containment area is moved to reduce the volume until the pressure starts to rise. The percentage of open cells is calculated from the amount of foam exterior volume which does not let air flow into the cells (i.e. a one hundred percent (100%) closed cell volume calculates the same a the foam exterior volume and zero percent (0%) calculates the same as the containment volume).

Also for the purpose of definition in this specification, the term fragrance is a compound which is added to the foam for the purpose of producing a scent (and usually no other purpose) and when added to the foam produces an odor which is associated with the foam and can be perceived through the sense of smell by human or animal. Generally a fragrance is pleasant or sweet smelling, but this need is not an absolute requirement. For example, perhaps certain odors are known to inhibit some types of behavior (i.e. chewing) in some animals. This odor may not be pleasant or fragrant to either animals or humans.

Many other products, such as a decongestant, a pesticide, a germicide or a disinfecting agent may have fragrances associated with the functionality of the product. However, for the purposes of this specification the fragrance compounds of the product are what is important, not the functionality of the product. Moreover, typically the fragrance compounds are utilized in the present invention at such a low additive levels that the normal functionality of the product may not be obtained at those additive levels.

The fragrant volatile material should be in an amount sufficient to impart the desired activity when exposed to the selected environment. In general, the volatile material is in an amount from about 0.001 to 5% by weight of the total composition, preferably 0.001 to 1%. While the active volatile material may have other uses for the purpose of this specification all volatile materials utilized are utilized for the purpose of fragrance.

It may also be possible to disperse scented particles into the foam. These scented particles which are dispersed in the foam may be frangible microcapsules containing a fragrance. Such microcapsules are available commercially from several sources and are also described in U.S. Pat. Nos. 2,969,330, 3,341,466, 3,516,943 and 3,415,758, which are hereby incorporated by reference.

The use of microcapsules can be particularly desirable because release of the scent may be further retarded and thus extended over a long period of time. When the frangible microcapsules are subjected to pressure, heat or moisture the capsules rupture, releasing the fragrance. In this manner release of the fragrance may be prolonged over an extended period of time. Handling of the foam during use will fracture some of the microcapsules thus liberating the fragrance. After being placed in use, perhaps as cushioning material and the initial scent has dissipated, the fragrance will continue to be released whenever the microcapsules are subjected to changes in pressure, moisture or heat. For example, merely squeezing a cushioning foam will result in liberation of the fragrance, as the pressure ruptures some of the microcapsules. The composition and thickness of the microcapsule coating may be adjusted to provide the desired fragrance release based upon anticipated factors such as maximum temperature and pressure.

Alternatively, the scented particles may be composed of bone material, clay or charcoal that have been treated with a fragrance. Such particles do not, of course, exhibit such a prolonged fragrance release characteristics of the microcapsules. Their utilization does, however, produce a foam product having a fragrance release time substantially longer than that exhibited by a foam which has had fragrance added directly to it during its manufacture This delay is a result of the slow adsorption properties of materials such as bone material, clay and charcoal. Fragrance that has been added to these carriers is released slowly to the surrounding atmosphere, thereby producing a time delay effect in the release. The scented particles are generally 200 mesh or finer to facilitate the dispersing from the hopper into the foam ingredient mixture. Experiments on possible carriers for the fragrance show Attapulgus clay, Western Bentonite and Southern Bentonite as excellent carriers.

Fragrance may be imparted to the foam by adding microcapsules containing the fragrance or particles carrying the fragrance or the fragrance itself to the virgin batch or the reprocessed batch. However if microcapsules are added during the manufacture of the foam, most of the capsules will rupture due to the heat and pressure created in the processing. Therefore, much of the fragrance is immediately liberated.

Two disadvantages may result from the use of any type of particles, including microspheres; 1) the immediate liberation of fragrance, which is undesirable; and 2) the particles may cause foam cell nucleation and thus foam formation problems. If it is not possible to produce a substantially closed cell foam with the use of particles, then either the fragrance should be used directly or the fragrance should be incorporated into the foam in a concentrate form.

U.S. Pat. No. 4,694,027, previously mentioned in the specification, hereby incorporated by reference, relates a process for preparing a substantially closed cell olefin polymer foam having dimensional stability.

U.S. Pat. No. 4,824,720, also hereby incorporated by reference discloses a method for producing closed cell foams particularly suitable for use in packaging applications comprising a plurality of coalesced strands or profiles of a foamed thermoplastic composition.

U.S. Pat. No. 4,824,720 states that blending of various components in order to provide a suitable thermoplastic composition for melt extrusion to prepare the coalesced extruded strand foams of the present invention is accomplished according to known techniques in the art. Suitably, a mixer, extruder or other suitable blending device is employed to obtain a homogeneous melt. An extruder or any other suitable device is then employed to incorporate a known volatile blowing agent and any additional agents. The molten extrudate is then forced through a die plate comprising numerous small holes in a suitably desired spatial arrangement or alternatively an array of slits, desirably in an oscillating form such as a sine wave, honeycomb, square saw tooth or triangular saw tooth wave pattern. Alternately in the use of holes in the die face plate, various geometric shapes particularly non-circular shapes, such as X-, cross- or star-shaped geometry may be employed.

The foam may be foamed at the die as it enters an atmosphere of lower pressure and may be a variety of shapes such as a coalesced strand foam or a unitary homogeneous extruded shape. Alternatively, it is known in the art to produce an expandable particle containing a volatile blowing agent by suppressing foaming upon extrusion from the die. The expandable particle may then be later expanded, usually with steam or hot air. U.S. Pat. Nos. 4,912,140: 4,866,098 and 4,839,396, hereby incorporated by reference, relate to expandable and expanded alkenyl aromatic polymer particles.

The following examples are by weight unless otherwise stated.

EXAMPLE 1

An ethylene-acrylic acid copolymer (3.0 weight percent acrylic acid - EAA-3150 available from The Dow Chemical Company) was run similarly to Example 1 in U.S. Pat. No. 4,824,720 using 19 pph (parts per hundred parts of ethylene-acrylic acid copolymer) of HCFC-142b (1-chloro-1,1-difluoroethane) as a blowing agent. Talc was present at about 0.5 pph as an additive, as was IRGANOX 1010 (obtained from Ciba-Geigy Corp., Hawthorne, N.Y.) at about 0.5 pph. Polyiff 272 (called "Mossy Pines") was obtained from International Flavors & Fragrances, Inc., New York, N.Y. and is polyethylene pellets containing twenty percent (20%) of a volatile oil fragrance in the pellets.

The polymer rate is started at 600 pounds per hour and the pellets are added at a rate of 1.7 pounds per hour. Thus the actual amount of fragrance in the foam, based on input, is 0.057 percent. The pressure of the gel going into the die was 525 pounds per square inch and the temperature was 100.4° C.

The fragrance was overpowering to the whole immediate ambient area upon exit from the die and foaming. No effect was observed in the physical properties of the foam. The coalesced foam plank still had the same cell size (0.6 mm (millimeters)), density 2.05 lb/ft3 (pounds per cubic foot) and overall size 2 inches by 24 inches by 9 feet.

Three weeks after making the foam the fragrance is still extremely strong and can be smelled even at a distance of ten feet from the foam in the open ambient atmosphere.

EXAMPLE 2

Example 1 was run again using the same basic ingredients, except fragrance. For this run Polyiff 286, called "Fresh Outdoors," (obtained from International Flavors & Fragrances, Inc., New York, N.Y. as a twenty percent (20%) volatile oil fragrance in polyethylene pellets) was used.

The polymer rate is started at 400 pounds per hour and the fragrance pellets are added at a rate of 0.27 pounds per hour. Thus the actual amount of fragrance in the foam, based on input, is 0.014 percent.

The fragrance noted by smell was a "soapy" fragrance at the die and the immediate ambient area near the die.

The foam retained the smell even after two weeks.

EXAMPLE 3

Example 1 was run yet again using the same basic ingredients, except fragrance. For this run Polyiff 718, called "Leather," (obtained from International Flavors & Fragrances, Inc., New York, N.Y. as a twenty percent (20%) volatile oil fragrance in polyethylene pellets) was used.

The polymer rate is started at 400 pounds per hour and the pellets are added at a rate of 0.10 pounds per hour. Thus the actual amount of fragrance in the foam, based on input, is 0.005 percent.

The fragrance was noted at the die upon extrusion.

The fragrance was still present upon smelling the foam, and when the foam was cut the fragrance was even more noticeable. These observations were still true even after the foam had been aged for a period of two weeks.

As can be seen by the Examples, as little as 0.005 percent of an actual fragrant compound can provide a fragrance for a substantially closed cell thermoplastic foam.

The foams of the present invention have a variety of uses. For example, a substantially closed cell polystyrene foam with an incorporated fragrance used for floral craft purposes could release that fragrance when flowers are pushed into the foam. Substantially closed cell foams with an incorporated fragrance could be used as air fresheners. Various consumer products, such as surf boards, toys and life jackets could utilize the substantially closed cell foams with an incorporated fragrance to slowly release the fragrance over a period of months or years. Also substantially closed cell foams with an incorporated fragrance can be used as packaging materials (usually as a cushioning material) and allow a slow release of the fragrance into the enclosed container. A person upon opening the container would then immediately smell the fragrance.

Having described the invention in detail and by reference to preferred embodiments thereof, it will be apparent that modifications and variations are possible without departing from the scope of the invention defined in the appended claims.

What is claimed is:

1. An extruded fragrant thermoplastic foam comprising a substantially closed cell thermoplastic foam and a fragrance which has been incorporated into the substantially closed cell foam as an additive during extrusion of the substantially closed cell thermoplastic foam.

2. An extruded fragrant thermoplastic foam, as recited in claim 1, wherein the substantially closed cell thermoplastic foam is at least eighty percent closed cell.

3. An extruded fragrant thermoplastic foam, as recited in claim 1, wherein the substantially closed cell thermoplastic foam is at least ninety percent closed cell.

4. An extruded fragrant thermoplastic foam, as recited in claim 1, wherein the fragrance is present in an amount of about 0.001 weight percent to about five weight percent based thermoplastic foam weight 0.001 to by weight of the total composition, preferably 0.001 to 1%.

5. An extruded fragrant thermoplastic foam, as recited in claim 1, wherein the fragrance is present in an amount of about 0.001 weight percent to about one weight percent based thermoplastic foam weight.

6. An extruded fragrant thermoplastic foam, as recited in claim 1, wherein the substantially closed cell thermoplastic foam is a substantially closed cell polyolefin foam.

7. An extruded fragrant thermoplastic foam, as recited in claim 1, wherein the substantially closed cell thermoplastic foam is a substantially closed cell polystyrene foam.

8. An extruded fragrant thermoplastic foam, as recited in claim 1, wherein the substantially closed cell thermoplastic foam is a substantially closed cell ethylene/acrylic acid copolymer foam.

9. An extruded fragrant thermoplastic foam, as recited in claim 1, wherein the substantially closed cell thermoplastic foam is in the form of coalesced strands.

10. A process for making an extruded fragrant thermoplastic foam comprising the steps of:
    (a) heat plastifying a thermoplastic polymer resin:
    (b) admixing said heat plastified resin with
        (1) fragrance, and
        (2) a volatile blowing agent: and
    (c) activating said blowing agent to expand said admixture to a substantially closed-cell thermoplastic polymer foam.

11. A process for making an extruded fragrant thermoplastic foam, as recited in claim 10, wherein the substantially closed cell thermoplastic foam is at least eighty percent closed cell.

12. A process for making an extruded fragrant thermoplastic foam, as recited in claim 10, wherein the substantially closed cell thermoplastic foam is at least ninety percent closed cell.

13. A process for making an extruded fragrant thermoplastic foam, as recited in claim 10, wherein the the fragrance is present in an amount of about 0.001 weight percent to about five weight percent based thermoplastic foam weight.

14. A process for making an extruded fragrant thermoplastic foam, as recited in claim 10, wherein the the fragrance is present in an amount of about 0.001 weight percent to about one weight percent based thermoplastic foam weight.

15. A process for making an extruded fragrant thermoplastic foam, as recited in claim 10, wherein the thermoplastic polymer resin is a polyolefin resin.

16. A process for making an extruded fragrant thermoplastic foam, as recited in claim 10, wherein the thermoplastic polymer resin is a polystyrene resin.

17. A process for making an extruded fragrant thermoplastic foam, as recited in claim 10, wherein the thermoplastic polymer resin is an ethylene/acrylic acid copolymer resin.

18. An extruded fragrant thermoplastic foam, as recited in claim 1, wherein the substantially closed cell thermoplastic foam is in the form of coalesced strands.

* * * * *

UNITED STATES PATENT AND TRADEMARK OFFICE
CERTIFICATE OF CORRECTION

PATENT NO. : 5,109,029

DATED : April 28, 1992

INVENTOR(S) : Bruce A. Malone

It is certified that error appears in the above-identified patent and that said Letters Patent is hereby corrected as shown below:

Column 9, line 28, before "by" insert --5%--.

Column 10, line 9, agent: should correctly appear -- agent; --.

Signed and Sealed this

Tenth Day of August, 1993

Attest:

MICHAEL K. KIRK

*Attesting Officer*  *Acting Commissioner of Patents and Trademarks*